(12) United States Patent
Dente et al.

(10) Patent No.: US 8,124,114 B2
(45) Date of Patent: Feb. 28, 2012

(54) FRAGRANCED POLYMER WITH MALODOR COUNTERACTANT

(75) Inventors: Stephen V. Dente, Oakland, NJ (US); Ann Robertson, Glen Rock, NJ (US)

(73) Assignee: Robertet, Inc., Oakland, NJ (US)

( * ) Notice: Subject to any disclaimer, the term of this patent is extended or adjusted under 35 U.S.C. 154(b) by 849 days.

(21) Appl. No.: 11/600,401

(22) Filed: Nov. 15, 2006

(65) Prior Publication Data

US 2007/0185228 A1 Aug. 9, 2007

Related U.S. Application Data

(60) Provisional application No. 60/737,560, filed on Nov. 17, 2005.

(51) Int. Cl.
*A61L 9/04* (2006.01)

(52) U.S. Cl. ........................... 424/405; 523/102

(58) Field of Classification Search ................. 424/405; 523/102
See application file for complete search history.

(56) References Cited

U.S. PATENT DOCUMENTS

| | | | | |
|---|---|---|---|---|
| 4,255,545 A | * | 3/1981 | Hurlock et al. | ............... 526/201 |
| 5,795,566 A | | 8/1998 | Joulain et al. | |
| 2004/0048955 A1 | | 3/2004 | Wada et al. | |

FOREIGN PATENT DOCUMENTS

| | | | |
|---|---|---|---|
| EP | 0210073 | | 7/1986 |
| EP | 0210073 | * | 1/1987 |
| GB | 2346900 | * | 8/2000 |
| WO | WO 00/64497 | | 11/2000 |
| WO | WO 01/16264 | | 3/2001 |

* cited by examiner

*Primary Examiner* — Marcos Sznaidman
(74) *Attorney, Agent, or Firm* — Fish & Richardson P.C.

(57) ABSTRACT

A malodor counteractant composition comprising beads of a water absorbent polymer and an aromachemical comprising at least two aldehydes. Optional ingredients include a solvent for the aromachemical and one or more surfactants.

10 Claims, No Drawings

FRAGRANCED POLYMER WITH MALODOR COUNTERACTANT

CROSS REFERENCE TO RELATED APPLICATION

This application claims the benefit of U.S. Provisional Application No. 60/737,560 filed on 17 Nov. 2005, and incorporated herein by reference.

BACKGROUND OF THE INVENTION

Water absorbent polymers are used in a wide variety of products, including air fresheners and room deodorizers containing a malodor counteractant. It is generally desired, for reasons of cost and to promote evaporation, to incorporate high levels of water into these products. However, high levels of solvents, solubilizers and/or surfactants are necessary in order to make fragrance oils miscible with water. With adequately high levels of such solvents, solubilizers or surfactants, the polymer forms clear beads with the water. If the amounts of such solvents, solubilizers or surfactants are inadequate, the polymer/water combination remains cloudy and/or grey in color, yielding a product that is not aesthetically appealing. Also, if not properly hydrated, the polymer does not function to prevent syneresis or to control the release of fragrance or malodor counteractant. However, with high levels of water and with corresponding high levels of solvents, solubilizers and surfactants, there is the risk that, as evaporation and release of volatile fragrance and malodor counteractant occurs, the polymer (along with non-volatile substances) will revert to its original opaque form. This often results in an unappealing sticky residue.

Accordingly, the object of this invention is to provide a clear, or mostly clear, aesthetically pleasing air freshening and/or an odor counteracting composition with a high water content which comprises a water absorbent polymer and low amounts of solvents, solubilizers or surfactants.

SUMMARY OF THE INVENTION

This invention provides compositions comprising (1) a water absorbent polymer, preferably in the form of beads, (2) one or more aromachemicals, (3) optionally, an organic solvent or solubilizing agent, (4) optionally, one or more surfactants, and (5) a major proportion of water.

The aromachemicals in the composition can be chosen so as to have relatively high solubility or miscibility with water. They should be chosen so as to maximize those with high levels of solubility or miscibility and minimize low levels of those which are relatively insoluble or immiscible. Preferably, the aromachemicals, solubilizers and surfactants are such that, as evaporation occurs during use, the composition will not exhibit syneresis or aesthetically unacceptable characteristics such as being sticky to the touch or being unattractively shriveled.

The term "aromachemicals" is intended to embrace fragrancing compounds and compositions as well as malodor counteracting compounds and compositions (regardless of whether these malodor counteractants themselves are fragrances).

DETAILED DISCLOSURE

The water absorbent polymers usable in these compositions may be one or more of the well-known polymers that are characterized by high water absorbency, i.e., the ability to absorb at least 10 times its weight of water. These polymers include crosslinked polyacrylates which are water absorbent such as those prepared from $\alpha,\beta$-ethylenically unsaturated monomers such as monocarboxylic acids, polycarboxylic acids, acrylamide and their derivatives, e.g. polymers having repeating units of acrylic acid, methacrylic acid, metal salts of acrylic acid, acrylamide, and acrylamide derivatives, along with various combinations of such repeating units as copolymers. Such derivatives include acrylic polymers which can be hydrophilic grafts of polymers such as polyvinyl alcohol. The aforementioned polymers are collectively referred to herein as "water absorbent polymers". Examples of suitable water absorbent polymers and processes, including gel polymerization processes, for preparing such polymers are well known in the art and are disclosed in U.S. Pat. Nos. 3,997,484; 4,093,776; 4,340,706; 4,446,261; 4,683,274; 4,459,396; 4,286,082; 4,857,610; 4,985,518; 5,145,906; 5,629,377; and 6,908,609, pertinent portions of which are incorporated herein by reference. In addition, see Buchholz, F L. and Graham, A. T., "Modern Superabsorbent Polymer Technology," John Wiley & Sons (1998). The degree of crosslinking can vary greatly depending upon the specific polymer material; however, in most applications the desired superabsorbent polymers are only lightly crosslinked, that is, the degree of crosslinking is such that the polymer can still absorb at least 10 times its weight of water or dilute aqueous solutions of soluble materials. For example, such polymers typically include less than about 0.2 mole percent crosslinking agent. Different morphological forms of the polymers are possible but bead forms are preferred for present purposes. Many of these polymers, regardless of the morphological form, are known for use as "super absorbents" and are commonly used in controlled release applications such as air fresheners, insecticides and personal hygiene products. Although the alkali metal and alkaline earth metal salts of the monomers can be used, the sodium salt is particularly preferred in the polymeric compositions.

A particularly useful highly water absorbent polymer is the sodium acrylate co-polymer sold in the form of beads under the trademark Hisobead® by Aekyung Specialty Chemicals Company, Ltd., Daejeon, South Korea. The product is a co-polymer of acrylamide and sodium acrylate.

The water-absorbent polymers are present in the inventive composition in an amount ranging from about 0.15% to 5.0% by weight. A preferred range is from 1.0% to 3.0%, more preferably about 1.2%. The amount of such polymers will depend on, inter alia, the absorbtive capacity of the particular polymer used.

A wide variety of aromachemicals can be used in the compositions of this invention. However, the invention has been found to be particularly useful with respect to the deodorant compositions disclosed in U.S. Pat. No. 5,795,566, which is incorporated herein by reference. These deodorant compositions comprise at least two aldehydes. At least one aldehyde must be selected from the group identified in "Class A" and at least one aldehyde must be selected from the group identified as "Class B". This technology is referred to by the term "Two Aldehyde Technology".

The first aldehyde is chosen from acyclic and non-terpenic aliphatic aldehydes, non-terpenic alicyclic aldehydes, terpenic aldehydes, aliphatic aldehydes substituted by an aromatic group, and bifunctional aldehydes (Class A). The second aldehyde is chosen from aldehydes possessing non-aromatic unsaturation carried by the carbon in the alpha position of the aldehyde function, aldehydes possessing an unsaturation in the alpha position of the aldehyde function conjugated with an aromatic ring, and aldehydes in which the function is carried by an aromatic ring (Class B).

The acyclic and non-terpenic aliphatic aldehydes of Class A are preferably: decanal; undecanal; dodecanal; undecene-10-al; 2-methyl-undecanal; 2,3,5,5-tetramethylhexanal; 1-formyl-2,4-dimethyl-2-cyclohexene; 1-formyl-3,5-dimethyl-4-cyclohexene; 1-formyl-2,3,5-trimethyl-4-cyclohexene; 1-formyl-2,4,6-trimethyl-3-cyclohexene; ([5.2.1.0]-tricyclo-8-decylidene)-4-butanal; 2,6,10-trimethyl-9-undecenal; (4-methyl-3-pentenyl)-4-cyclohexene-3-yl carboxaldehyde; 7-formyl-5-isopropyl-2-methyl-[2.2.2]-bicyclo-2-octene; and 2-formyl-8-dimethyl-1,2,3,4,5,6,7,8-octahydronaphthalene.

The terpenic aldehydes of Class A are preferably citronellal and campholenic aldehyde.

The aliphatic aldehydes substituted by an aromatic group of Class A are preferably α-methyl-3,4-methylenedioxyhydrocinnamic aldehyde; cyclamen aldehyde; lilial; canthoxal; phenylacetic aldehyde; 3-phenylpropionic aldehyde; and hydratropic aldehyde.

By "bifunctional aldehyde" in Class A is meant aldehydes possessing an additional function such as the ether-oxide or alcohol functions, preferably alkoxyacetaldehydes; ω-hydroxyaldehydes; (e.g., hydroxycitronellal); and ω-alkoxyaldehydes.

For Class B, the aldehydes which possess a non-aromatic type unsaturation carried by the carbon in the alpha position of the aldehyde function are preferably citral (neral and geranial); myrtenal; perilla aldehyde; and variously substituted 2-furyl carboxaldehydes.

The aldehydes in Class B which possess an ethylene unsaturation in the alpha position, itself conjugated with an aromatic ring, are preferably cinnamic aldehyde; amylcinnamic aldehyde; and hexylcinnamic aldehyde.

The aldehydes of Class B carried by an aromatic ring, which can be various substituted, are preferably benzaldehyde; anisic aldehyde; heliotropine; veratric aldehyde; vanillin; isovanillin; and ethylvanillin.

Typically, the aromachemicals used in the compositions of this invention will comprise a plurality—for example, up to 15 or more—of aldehydes from Class A and a plurality—for example, up to about 15—of aldehydes from Class B. A desirable aromachemical mixture would include α-methyl-3,4-methylene-dioxyhydrocinnamic aldehyde (Helional®) from Class A and amylcinnamic aldehyde (Jasmonal®) from Class B.

The amount of fragrance in the compositions of this invention ranges from about 0.5% to about 10% by weight, preferably from 1.5% to 5% by weight and more preferably about 3.0% by weight.

The organic solvent or solubilizing agent may be any substance generally recognized as suitable in the preparation of air fresheners or room deodorants. These include, for example, alkyl alcohols such as ethanol or isopropanol, ethers such as monopropyleneglycol methyl ether, or dipropyleneglycol methyl ether, carbitol or a glycol such as propylene glycol or dipropylene glycol. Preferable solvents include ethanol, ethyl phthalate, diethyl phthalate, benzyl benzoate, ethyl citrate and their various analogues.

The surfactants usable in these compositions may be any of the surfactants ordinarily used in the formulation of air fresheners and deodorizers. These include anionic surfactants, cationic surfactants, non-ionic surfactants, amphoteric surfactants, zwitterionic surfactants, and compatible mixtures thereof.

The preferred compositions of this invention include one or more organic solvents, and one or more surfactants. The preferred amount of such solvents ranges from about 0.5% to 10.0% by weight, more preferably from 1.5% to 5.0% by weight, with about 3.0% by weight being a desirable amount. The preferred total amount of surfactants ranges from about 1.0% by weight to 30% by weight, more preferably from 3.0% to 25% by weight, and most preferably from 10% to 17% by weight.

The composition of this invention are aqueous compositions comprising a major proportion of water. Preferably, the compositions comprise at least 60% water, more preferably from about 70% to about 90% water.

The following examples are exemplary formulations of the inventive composition. These examples are being presented for purposes of illustration only and it should be understood that further useful formulations falling within the scope of this invention and claims may be readily produced by persons skilled in the art, without deviating from the scope and spirit of the invention. Unless otherwise indicated, weight percents are to be understood as being the weight percent of the active portion of the referenced constituent.

EXAMPLES

Compositions according to this invention were prepared with the ingredients shown in Tables I, II, III and IV.

TABLE I

|                | Ex 1   | Ex 2   | Ex 3   | Ex 4   | Ex 5   | Ex 6   | Ex 7   |
|----------------|--------|--------|--------|--------|--------|--------|--------|
| Fragrance      | 3.00   | 3.00   | 3.00   | 3.00   | 3.00   | 3.00   | 3.00   |
| Eumulgin ® HPS | 2.50   | 3.00   | 3.00   | 2.00   | 2.00   | 3.00   | 2.00   |
| Amine Oxide    | 5.00   | 4.00   | 4.00   | 6.00   | 4.00   | 6.00   | 4.00   |
| Tween ® 80     | 2.00   | 1.50   | 2.50   | 1.50   | 1.50   | 2.50   | 1.50   |
| Sol Sri        | 2.50   | 3.00   | 2.00   | 2.00   | 3.00   | 2.00   | 2.00   |
| Ethanol        | 3.00   | 3.00   | 3.00   | 3.00   | 3.00   | 3.00   | 3.00   |
| DI Water       | 80.60  | 81.10  | 81.10  | 81.10  | 82.10  | 79.10  | 83.10  |
| Hisobead ® beads | 1.40 | 1.40   | 1.40   | 1.40   | 1.40   | 1.40   | 1.40   |
|                | 100.00 | 100.00 | 100.00 | 100.00 | 100.00 | 100.00 | 100.00 |
|                | Ex 8   | Ex 9   | Ex 10  | Ex 11  | Ex 12  | Ex 13  | Ex 14  |
| Fragrance      | 3.00   | 3.00   | 3.00   | 3.00   | 3.00   | 3.00   | 3.00   |
| Eumulgin ® HPS | 2.00   | 3.00   | 2.00   | 2.00   | 3.00   | 3.00   | 2.00   |
| Amine Oxide    | 6.00   | 4.00   | 4.00   | 4.00   | 4.00   | 6.00   | 6.00   |
| Tween ® 80     | 2.50   | 1.50   | 2.50   | 2.50   | 2.50   | 1.50   | 2.50   |
| Sol Sri        | 3.00   | 2.00   | 2.00   | 3.00   | 3.00   | 3.00   | 2.00   |
| Ethanol        | 3.00   | 3.00   | 3.00   | 3.00   | 3.00   | 3.00   | 3.00   |

TABLE I-continued

|  |  |  |  |  |  |  |  |
|---|---|---|---|---|---|---|---|
| DI Water | 79.10 | 82.10 | 82.10 | 81.10 | 80.10 | 79.10 | 80.10 |
| Hisobead ® beads | 1.40 | 1.40 | 1.40 | 1.40 | 1.40 | 1.40 | 1.40 |
|  | 100.00 | 100.00 | 100.00 | 100.00 | 100.00 | 100.00 | 100.00 |

|  | Ex 15 | Ex 16 | Ex 17 | Ex 18 | Ex 19 | Ex 20 | Ex 21 |
|---|---|---|---|---|---|---|---|
| Fragrance | 3.00 | 3.00 | 3.00 | 3.00 | 3.00 | 3.00 | 3.00 |
| Eumulgin ® HPS | 3.00 | 2.00 | 2.50 | 3.00 | 1.00 | 1.50 | 1.25 |
| Amine Oxide | 6.00 | 6.00 | 5.00 | 6.00 | 2.00 | 2.00 | 2.50 |
| Tween ® 80 | 2.50 | 1.50 | 2.00 | 1.50 | 1.00 | 1.50 | 1.25 |
| Sol Sri | 3.00 | 3.00 | 2.50 | 2.00 | 1.00 | 1.00 | 1.25 |
| Ethanol | 3.00 | 3.00 | 3.00 | 3.00 | 3.00 | 3.00 | 3.00 |
| DI Water | 78.10 | 80.10 | 80.60 | 80.10 | 87.60 | 86.60 | 86.35 |
| Hisobead ® beads | 1.40 | 1.40 | 1.40 | 1.40 | 1.40 | 1.40 | 1.40 |
|  | 100.00 | 100.00 | 100.00 | 100.00 | 100.00 | 100.00 | 100.00 |

|  | Ex 22 | Ex 23 | Ex 24 | Ex 25 | Ex 26 | Ex 27 | Ex 28 |
|---|---|---|---|---|---|---|---|
| Fragrance | 3.00 | 3.00 | 3.00 | 3.00 | 3.00 | 3.00 | 3.00 |
| Eumulgin ® HPS | 1.00 | 1.50 | 1.25 | 1.50 | 1.50 | 3.00 | 1.00 |
| Amine Oxide | 3.00 | 2.00 | 2.50 | 3.00 | 3.00 | 6.00 | 2.00 |
| Tween ® 80 | 1.50 | 1.00 | 1.25 | 1.00 | 1.50 | 2.50 | 1.50 |
| Sol Sri | 1.00 | 1.50 | 1.25 | 1.00 | 1.50 | 2.00 | 1.50 |
| Ethanol | 3.00 | 3.00 | 3.00 | 3.00 | 3.00 | 3.00 | 3.00 |
| DI Water | 86.10 | 86.60 | 86.35 | 86.10 | 85.10 | 79.10 | 86.60 |
| Hisobead ® beads | 1.40 | 1.40 | 1.40 | 1.40 | 1.40 | 1.40 | 1.40 |
|  | 100.00 | 100.00 | 100.00 | 100.00 | 100.00 | 100.00 | 100.00 |

|  | Ex 29 | Ex 30 | Ex 31 | Ex 32 | Ex 33 | Ex 34 | Ex 35 |
|---|---|---|---|---|---|---|---|
| Fragrance | 3.00 | 3.00 | 3.00 | 3.00 | 3.00 | 3.00 | 3.00 |
| Eumulgin ® HPS | 1.00 | 2.00 | 1.00 | 2.00 | 1.00 | 2.00 | 1.00 |
| Amine Oxide | 3.00 | 3.00 | 4.00 | 3.00 | 4.00 | 4.00 | 3.00 |
| Tween ® 80 | 1.00 | 1.00 | 1.00 | 3.00 | 3.00 | 3.00 | 3.00 |
| Sol Sri | 0.00 | 0.00 | 0.00 | 0.00 | 0.00 | 0.00 | 0.00 |
| Ethanol | 3.00 | 3.00 | 3.00 | 3.00 | 3.00 | 3.00 | 3.00 |
| DI Water | 87.40 | 86.40 | 86.40 | 84.40 | 84.40 | 83.40 | 85.40 |
| Hisobead ® beads | 1.60 | 1.60 | 1.60 | 1.60 | 1.60 | 1.60 | 1.60 |
|  | 100.00 | 100.00 | 100.00 | 100.00 | 100.00 | 100.00 | 100.00 |

|  | Ex 36 | Ex 37 |
|---|---|---|
| Fragrance | 3.00 | 3.00 |
| Eumulgin ® HPS | 1.50 | 2.00 |
| Amine Oxide | 3.50 | 4.00 |
| Tween ® 80 | 2.00 | 1.00 |
| Sol Sri | 0.00 | 0.00 |
| Ethanol | 3.00 | 3.00 |
| DI Water | 85.40 | 85.40 |
| Hisobead ® beads | 1.60 | 1.60 |
|  | 100.00 | 100.00 |

TABLE II

|  | Ex 38 | Ex 39 | Ex 40 | Ex 41 | Ex 42 | Ex 43 | Ex 44 |
|---|---|---|---|---|---|---|---|
| Fragrance | 3.00 | 3.00 | 3.00 | 3.00 | 3.00 | 3.00 | 3.00 |
| Amine Oxide | 2.00 | 3.00 | 3.00 | 3.00 | 2.50 | 3.00 | 3.00 |
| Cremephor ® | 1.50 | 1.00 | 1.50 | 1.00 | 1.25 | 1.00 | 1.00 |
| Eumulgin ® HPS | 1.50 | 1.00 | 1.00 | 1.00 | 1.25 | 1.50 | 1.50 |
| Neodol ® | 1.00 | 1.50 | 1.50 | 1.00 | 1.25 | 1.50 | 1.00 |
| Ethanol | 3.00 | 3.00 | 3.00 | 3.00 | 3.00 | 3.00 | 3.00 |
| DI Water | 86.60 | 86.10 | 85.60 | 86.60 | 86.35 | 85.60 | 86.10 |
| Beads | 1.40 | 1.40 | 1.40 | 1.40 | 1.40 | 1.40 | 1.40 |
|  | 100.00 | 100.00 | 100.00 | 100.00 | 100.00 | 100.00 | 100.00 |

|  | Ex 45 | Ex 46 | Ex 47 | Ex 48 | Ex 49 | Ex 50 | Ex 51 |
|---|---|---|---|---|---|---|---|
| Fragrance | 3.00 | 3.00 | 3.00 | 3.00 | 3.00 | 3.00 | 3.00 |
| Amine Oxide | 2.00 | 2.00 | 2.00 | 2.00 | 3.00 | 2.00 | 3.00 |
| Cremephor ® | 1.50 | 1.00 | 1.50 | 1.00 | 1.50 | 1.00 | 1.50 |

TABLE II-continued

| | | | | | | | |
|---|---|---|---|---|---|---|---|
| Eumulgin ® HPS | 1.00 | 1.00 | 1.00 | 1.50 | 1.00 | 1.00 | 1.50 |
| Neodol ® | 1.50 | 1.00 | 1.00 | 1.00 | 1.00 | 1.50 | 1.50 |
| Ethanol | 3.00 | 3.00 | 3.00 | 3.00 | 3.00 | 3.00 | 3.00 |
| DI Water | 86.60 | 87.60 | 87.10 | 87.10 | 86.10 | 87.10 | 85.10 |
| Beads | 1.40 | 1.40 | 1.40 | 1.40 | 1.40 | 1.40 | 1.40 |
| | 100.00 | 100.00 | 100.00 | 100.00 | 100.00 | 100.00 | 100.00 |

| | Ex 51 | Ex 53 | Ex 54 |
|---|---|---|---|
| Fragrance | 3.00 | 3.00 | 3.00 |
| Amine Oxide | 2.00 | 2.00 | 3.00 |
| Cremephor ® | 1.00 | 1.50 | 1.50 |
| Eumulgin ® HPS | 1.50 | 1.50 | 1.50 |
| Neodol ® | 1.50 | 1.50 | 1.00 |
| Ethanol | 3.00 | 3.00 | 3.00 |
| DI Water | 86.60 | 86.10 | 85.60 |
| Beads | 1.40 | 1.40 | 1.40 |
| | 100.00 | 100.00 | 100.00 |

TABLE III

| | Ex 55 | Ex 56 | Ex 57 | Ex 58 | Ex 59 |
|---|---|---|---|---|---|
| Fragrance | 3.00 | 3.00 | 3.00 | 3.00 | 3.00 |
| Amine Oxide | 2.50 | 3.50 | 2.50 | 3.50 | 3.50 |
| Tween ® 80 | 3.50 | 2.00 | 2.00 | 3.50 | 2.00 |
| Eumulgin ® HPS | 1.50 | 1.50 | 0.75 | 0.75 | 0.75 |
| Ethanol | 3.00 | 3.00 | 3.00 | 3.00 | 3.00 |
| DI Water | 85.10 | 85.60 | 87.35 | 84.85 | 86.35 |
| Beads | 1.40 | 1.40 | 1.40 | 1.40 | 1.40 |
| | 100.00 | 100.00 | 100.00 | 100.00 | 100.00 |

| | Ex 60 | Ex 61 | Ex 62 | Ex 63 |
|---|---|---|---|---|
| Fragrance | 3.00 | 3.00 | 3.00 | 3.00 |
| Amine Oxide | 2.50 | 3.00 | 3.50 | 2.50 |
| Tween ® 80 | 2.00 | 2.75 | 3.50 | 3.50 |
| Eumulgin ® HPS | 1.50 | 1.13 | 1.50 | 0.75 |
| Ethanol | 3.00 | 3.00 | 3.00 | 3.00 |
| DI Water | 86.60 | 85.72 | 84.10 | 85.85 |
| Beads | 1.40 | 1.40 | 1.40 | 1.40 |
| | 100.00 | 100.00 | 100.00 | 100.00 |

TABLE IV

| | Ex 64 | Ex 65 | Ex 66 | Ex 67 | Ex 68 |
|---|---|---|---|---|---|
| Fragrance | 3.00 | 3.00 | 3.00 | 3.00 | 3.00 |
| Amine Oxide | 1.75 | 2.00 | 2.00 | 2.00 | 2.00 |
| Cremephor ® | 1.00 | 1.00 | 2.00 | 2.00 | 1.00 |
| Eumulgin ® HPS | 0.75 | 0.75 | 0.75 | 1.50 | 1.50 |
| Tomadol ® | 1.00 | 2.00 | 1.00 | 2.00 | 1.00 |
| Ethanol | 3.00 | 3.00 | 3.00 | 3.00 | 3.00 |
| DI Water | 88.10 | 86.85 | 86.85 | 85.10 | 87.10 |
| Beads | 1.40 | 1.40 | 1.40 | 1.40 | 1.40 |
| | 100.00 | 100.00 | 100.00 | 100.00 | 100.00 |

| | Ex 69 | Ex 70 | Ex 71 | Ex 72 |
|---|---|---|---|---|
| Fragrance | 3.00 | 3.00 | 3.00 | 3.00 |
| Amine Oxide | 1.75 | 1.75 | 1.75 | 1.88 |
| Cremephor ® | 1.00 | 2.00 | 2.00 | 1.50 |
| Eumulgin ® HPS | 1.50 | 0.75 | 1.50 | 1.13 |
| Tomadol ® | 2.00 | 2.00 | 1.00 | 1.50 |
| Ethanol | 3.00 | 3.00 | 3.00 | 3.00 |
| DI Water | 86.35 | 86.10 | 86.35 | 86.59 |
| Beads | 1.40 | 1.40 | 1.40 | 1.40 |
| | 100.00 | 100.00 | 100.00 | 100.00 |

In the foregoing compositions, the fragrance used was a proprietary formulation employing the Two Aldehyde Technology. The fragrance comprises a number of ingredients conforming to Class A in U.S. Pat. No. 5,796,566 and a number of ingredients conforming to Class B in said patent. The Hisobead® polymer beads are made of acrylamide/sodium acrylate co-polymer and identified by CAS No. 25085-02-3. These co-polymer beads are manufactured by Aekyung Specialty Chemicals Company, Ltd., of Daejeon, South Korea.

The various surfactants in these formulations are as follows:

Eumulgin® HPS is a blend of ethoxylated alcohols made by Cognis Corporation (Cincinnati, Ohio). The blend is: coceth-7, a polyethylene glycol derivative of coconut alcohol; PPG-1-PEG9 lauryl glycol ether, which is the ethoxylated/propoxylated ether of a lauryl epoxide and ethylene glycol reaction product; and PEG-40 hydrogenated castor oil.

The amine oxide is lauryl dimethylamine oxide sold under the name Surfox® Lo Special by Surfactants, Inc. (Middlesex, N.J.).

Tween® 80 is polysorbate 80, sold by Degussa Corporation (Parsippany, N.J.).

Sol Sri is solubilisant LRI. A blend of ethoxylated ethers and PEG-40 hydrogenated castor oil sold by LCW USA, (South Plain Field, N.J.).

Cremophor® is Cremophor RH 40, which is a PEG-40 hydrogenated castor oil sold by BASF Corporation (Florham Park, N.J.).

Neodol® is Neodol 91-8, and ethoxylated alcohol sold by Shell Chemical LP (Houston, Tex.).

Tomadol® is Tomadol 25-12, an ethoxylated $C_{12-15}$ alcohol with 12 moles of ethoxylation, sold by Tomah Products (Milton, Wis.).

The symbol ® indicates that the name is believed to be a trademark, but does not imply registration in any particular country.

The general procedure for manufacturing these compositions is as follows: The fragrance is mixed with ethanol and agitated until uniform. The various surfactants are then added. It is preferable that the surfactants be added individually, but there is no specified order. After the surfactants have been uniformally blended into the ethanol solution, water is added and then mixed until uniformity is obtained. Lastly, the Hisobead beads are added and the mixture is agitated until the beads become fully hydrated.

It is to be understood that, while the invention has been described in conjunction with the detailed description thereof, the foregoing description is intended to illustrate and not limit the scope of the invention, which is defined by the scope of the appended claims. Other aspects, advantages and modifications are within the scope of the following claims.

We claim:

1. An aqueous composition comprising:
   (1) a water absorbent co-polymer in the form of beads and comprising units of sodium acrylate,
   (2) an aromachemical comprising
      (a) one or more compounds selected from the group consisting of: decanal; undecanal; dodecanal; undecene-10-al; 2-methyl-undecanal; 2,3,5,5-tetramethylhexanal; 1-formyl-2,4-dimethyl-2-cyclohexene; 1-formyl-3,5-dimethyl-4-cyclohexene; 1-formyl-2,3,5-trimethyl-4-cyclohexene; 1-formyl-2,4,6-trimethyl-3-cyclohexene; ([5.2.1.0]-tricyclo-8-decylidene)-4-butanal; 2,6,10-trimethyl-9-undecenal; (4-methyl-3-pentenyl)-4-cyclohexene-3-yl carboxaldehyde; 7-formyl-5-isopropyl-2-methyl-[2.2.2]-bicyclo-2-octene; and 2-formyl-8-dimethyl-1,2,3,4,5,6,7,8-octahydronaphthalene; citronellal; campholenic aldehyde; α-methyl-3,4-methylenedioxyhydrocinnamic aldehyde; cyclamen aldehyde; lilial; canthoxal; phenylacetic aldehyde; 3-phenylpropionic aldehyde; hydratropic aldehyde; α-methyl-3,4-methylenedioxyhydrocinnamic aldehyde; cyclamen aldehyde; lilial; canthoxal; phenylacetic aldehyde; 3-phenylpropionic aldehyde; hydratropic aldehyde; alkoxyacetaldehydes; ω-hydroxyaldehydes; and ω-alkoxyaldehydes, and
      (b) one or more compounds selected from the group consisting of: myrtenal; perilla aldehyde; variously substituted 2-furyl carboxaldehydes; cinnamic aldehyde; amylcinnamic aldehyde; hexylcinnamic aldehyde; benzaldehyde; anisic aldehyde; heliotropine; veratric aldehyde; vanillin; isovanillin; and ethylvanillin,
   (3) optionally, an organic solvent or solubilizing agent,
   (4) optionally, a surfactant, and
   (5) a major proportion of water.

2. A composition according to claim 1 in which the co-polymer comprises acrylamide.

3. A composition according to claim 1 in which the co-polymer beads are present in an amount ranging from about 0.15% to about 5.0% by weight and the fragrance is present in an amount ranging from about 0.5% to about 10% by weight.

4. A composition according to claim 3 which comprises a solvent present in an amount of from about 0.5% to about 10.0% by weight.

5. A composition according to claim 4 in which the solvent is present in an amount of from 1.5% to 5.0% by weight.

6. A composition according to claim 5 in which the solvent is selected from the group consisting of ethanol, ethyl phthalate, diethyl phthalate, benzyl benzoate and ethyl citrate.

7. A composition according to claim 6 in which the solvent is ethanol.

8. A composition according to claim 3 which comprises one or more surfactants in a total amount of from about 1.0% by weight to about 30% by weight.

9. A composition according to claim 8 in which the surfactants are present in an amount ranging from 10% to 17%.

10. A composition according to claim 1 in which the fragrance comprises α-methyl-3,4-methylene-dioxyhydrocinnamic aldehyde and amylcinnamic aldehyde.

* * * * *